United States Patent [19]

Nudelman et al.

[11] Patent Number: 5,200,553
[45] Date of Patent: Apr. 6, 1993

[54] BIOLOGICALLY ACTIVE CARBOXYLIC ACID ESTERS

[75] Inventors: Abraham Nudelman, Rehovot; Matitiahu Shaklai; Ada Rephaeli, both of Tel Aviv, all of Israel

[73] Assignee: Kupat Holim Health Insurance Institution of the General Federation of Labor, Tel Aviv, Israel

[21] Appl. No.: 223,595

[22] Filed: Jul. 25, 1988

[30] Foreign Application Priority Data

Jul. 30, 1987 [IL]  Israel ........................................ 83389
Jul. 11, 1988 [IL]  Israel ........................................ 87072

[51] Int. Cl.$^5$ ............................................. C07C 67/02
[52] U.S. Cl. .................................. 560/263; 560/174; 560/178; 560/189; 560/254; 549/71; 514/512; 514/547; 514/548; 514/533
[58] Field of Search ............... 560/263, 174, 178, 254, 560/105, 112, 189; 260/410.6; 549/62, 71, 479; 514/512, 547, 548, 533; 558/270, 271, 276, 273

[56] References Cited

U.S. PATENT DOCUMENTS

| | | | |
|---|---|---|---|
| 3,293,220 | 12/1966 | Minami et al. | 560/254 X |
| 3,499,028 | 3/1970 | McIver | 560/210·X |
| 3,720,706 | 3/1973 | Lapporte et al. | 560/238 |
| 4,012,256 | 3/1977 | Kensler, Jr. et al. | 560/263 |
| 4,541,944 | 9/1985 | Sanderson | 560/263 x |

FOREIGN PATENT DOCUMENTS

| | | | |
|---|---|---|---|
| 0018259 | 10/1980 | European Pat. Off. | |
| 1386096 | 7/1965 | France | |
| 1540418 | 9/1968 | France | |
| 877243 | 9/1961 | United Kingdom | |
| 1177442 | 1/1970 | United Kingdom | 560/254 |

OTHER PUBLICATIONS

Takeuchi et al., Chemical Abstracts, vol. 93:210255h 1980.
W. L. Badger, "Apparatus, Plant Equipment and Unit Operations", Chemical Abstracts, vol. 31, No. 18, Sep. 20, 1937, pp. 1036-1037.
Prasad et al., "Role of Cyclic AMP in Differentiation of Human Neuroblastoma Cells in Culture", Cancer 36, pp. 1338-1343 (1975).
Collins et al., "Terminal Differentiation of Human Promyelocytic Leukemia Cells Induced by Demithyl Sulfoxide and other Polar*".
Dexter et al., "Sodium Butyrate-Induced Alteration of Growth Properties and Glycogen Levels In Cultured Human Colon Carcinoma*".

(List continued on next page.)

Primary Examiner—Arthur C. Prescott
Assistant Examiner—Vivian Garner
Attorney, Agent, or Firm—Cushman, Darby & Cushman

[57] ABSTRACT

Biologically active carboxylic acid esters which promote antitumor or immune response are selected from the group consisting of compounds having formulas (I), (II) and (III):

$$XCH_2-CHX-CHX-C(=O)-O-Z \qquad (I)$$

$$CH_3-CO-CH_2-C(=O)-O-Z \qquad (II)$$

$$CH_3-CH_2-CO-C(=O)-O-Z \qquad (III)$$

wherein X is H, or one X only may be OH; Z is —CHR—O—(O=)C—R', R represents a member selected from the group consisting of hydrogen and alkyl, and R' represents a member of the group consisting of alkyl, aminoalkyl, aralkyl, aryl, alkoxy, aralkoxy and aryloxy, in which aryl by itself, and aryl in aralkyl, aralkoxy and aryloxy, are each selected from the group consisting of sub-groups (a) and (b), wherein (a) is unsubstituted phenyl, napthyl, furyl or thienyl, and (b) is phenyl, napthyl, furyl or thienyl, each of which is substituted by at least one substituent selected from the group consisting of alkyl, alkoxy or halogen, provided that in (I) when X is H and R' is propyl, then R is alkyl which contains at least three carbon atoms.

12 Claims, No Drawings

OTHER PUBLICATIONS

Augeron et al., "Emergence of Permanently Differentiated Cell Line in Culture after Treatment with Sodium Butyrate", Can. Res. 44*.

McIntyre et al., "Effects of Sodium Butyrate and DMA on Human Pancreatic Tumor Cell Lines*", Euro. J. Can. Clin. Oncol., vol. 20*.

Heifetz et al., "The Effect of Butyrate on Sulfated Glycoprotein Biosythesis by Human Kidney Tumor Cells", J. Bio. Chem., vol. 256*.

Stevens et al., "Associated Effects of Sodium Butyrate on Histone Acetylation and Estrogen Receptor in the Human Breast Cancer*".

Reese et al., "Control of Growth, Morphology, and Alkaline Phosphatase Activity by Butyrate and Related Short-Chain Fatty*".

MacIntyre, E. H. et al., "The Responses in Culture of Human Tumour Astrocytes and neuroblasts to $N^6,O^{2'}$-Dibutyryl Adenosine*".

Macher et al., "Studies on the Mechanism of Butyrate-Induced Morphological Changes in KB Cells", Exp. Cell Res., 117, 95–102 (1978).

Prasad, "Butyric Acid: A Small Fatty Acid with Diverse Biological Functions", Life Sci., vol. 27, pp. 1351–1358 (1980).

Novogrodsky et al., "Effect of Polar Organic Compounds on Leukemic Cells", Cancer, vol. 51, pp. 9–14 (1983).

Rephaeli et al., "Effect of the Cell Differentiation Inducers Butyrate, Retinoic Acid and Low Dose Cytosine Arabinoside on*".

Januszewicz et al., "Butyric Acid: Inhibition of Non-Leukemic and Chronic Myeloid Leukemia Granulocyte Macrophage Clonal Growth*".

Wheeler et al., "Orally Active Esters of Cephalosporin Antibiotics", J. Med. Chem., vol. 22, No. 6, pp. 657–661 (1979).

Daehne et al., "Acyloxymethyl Esters of Ampicillin", J. Med. Chem., vol. 13, No. 4, pp. 607–6122 (1970).

Bodin et al., "Bacampicillin: a New Orally Well-Absorbed Derivative of Ampicillin", Antimicrob. Ag. Chemother., vol. 8, pp. 518–525 (1975).

Foresta et al., "A New Cephalosporin Derivative (ST-21) Orally Administered in Laboratory Animals", Arzneim-Forsch./Drug. Res.*

Clayton et al., "BRL.8988 (Talampicillin), a Well-Absorbed Oral Form of Ampilicillin", Antimicrobial Ag. Chemotherapy, vol. 5.

Roholt, Antimicrob. Chemother. 3 (suppl. B):7.10 (1977).

"Developmental Therapeutics Program, Division of Cancer Treatment National Cancer Institute", NIH Publication 84-2635.

Miller et al., "Clinical Pharmacology of Sodium Butyrate in Patients with Acute Leukemia", Eur. J. Clin. Oncol., vol. 23*.

Fujimoto, Koichi et al., "Studies on Orally Active Cephalosporin Esters", J. Antibiotics, vol. XL, No. 3, pp. 370–384 (1987).

Man et al., "Boron Fluoride Catalyzed Addition of Aliphatic Anhydrides to Aldehydes", J. Am. Chem. Soc., vol. 72, pp. 847–848 (1950).

BIOLOGICALLY ACTIVE CARBOXYLIC ACID ESTERS

FIELD OF THE INVENTION

The present invention relates to biologically active carboxylic acid esters, pharmaceutical compositions containing them, methods for treating animals therewith, and the use of such esters for the manufacture of medicaments.

BACKGROUND OF THE INVENTION

Butyric acid is a non-toxic natural product found in butter in concentrations of up to approximately 5%. In the digestive system it is secreted as a product of microbial fermentation. In the colon it can reach mM concentrations.

It is known that butyric acid, whether in free form or more usually in the form of its alkali metal salts (hereinafter referred to as "butyric acid/salts"), displays antineoplastic activity. In particular, this activity is evidenced in the form of toxicity towards neoplastic cells, inhibition of cell proliferation, and induction of cytodifferentiation. Such activity has been demonstrated both in vitro and in vivo.

Thus, e.g. in a variety of tumor cells grown in vitro, there has been reported anti-tumor activity of butyric acid/salts due to the induction of morphological and biochemical changes. Some representative examples of affected cells derived from human sources are: neuroblastoma [Prasad and Kumar, Cancer 36:1338 (1975)]: leukemia [Collins et al. Proc. Natl. Acad. Sci. 75:2458 (1978)]; colon carcinoma [Dexter et al. Histochem. 16:137 (1984)] and Augeron and Laboisse, Cancer Res. 44:3961 (1984)]; pancreatic carcinoma [McIntyres et al, Euro. J. Cancer Clin. Onc. 20:265 (1984)]; kidney tumor cells [Heifetz et al. J. Biol. Chem. 256:6529 (1981)]; breast cancer [Stevens et al, Biochem. Biophys. Res. Comm. 119:132 (1984)]; prostatic carcinoma [Reese et al, Cancer Res. 45:2308 (1985)]; astrocytoma [McIntyre, J. Cell. Sci. 11:634 (1971)]; human epidermoid carcinoma [Marcher et al, Exp. Cell. Res. 117:95 (1978)]. Moreover, in all in vitro tests carried out by the present inventors, on leukemic cells isolated from myelogenous leukemic patients, butyric acid/salts was found to be the most potent cytotoxic and cytodifferentiating agent, being for example, more effective than retinoic acid, 1, 25-dihydroxy vitamin D and cytosine arabinoside.

Reported examples of in vivo application of butyric acid/salts are as follows. Patients with neuroblastoma received doses of up to 10 g./day, which produced no clinically detectable toxicity [Prasad, Life Sci. 27:1351 (1980)]. Treatment of a child with refractory acute myelogenous leukemia in relapse. with 0.5 g./kg./day, resulted in partial and temporary remission without detectable toxic effects [Novogrodsky et al. Cancer 51:9 (1983)]. Furthermore, the present inventors have treated a patient with acute myelogenous leukemia in relapse, with 1.0 g./kg./day for 10 days and 1.5 g./kg./day for an additional 6 days; the clinical follow up showed no adverse reaction [Rephaeli et al, Blood 68:192a (1986)]. Clinical trials with high dosages of butyric acid/salts resulted in no toxicity.

The selectivity of butyric acid/salts was demonstrated, in hitherto unpublished work (by M. Shaklai and E. Januszewiez) by inhibition of colony forming units, granulocytes and macrophages (CFU-GM), grown in soft agar, obtained from normal bone marrow and from peripheral blood of leukemic patients.

The main disadvantages of butyric acid/salts are a low intrinsic potency, a long induction period (4–5 days in vivo. 48 hours in vitro), a high clearance and rapid metabolization. Also, it is usually administered by infusion to peripheral veins, in high doses up to 1.5 g./kg./day, which procedure requires hospitalization, and is generally inconvenient for patients. Moreover, because of the high dosage, fluid overload and mild alkalosis may occur. Additionally, the unpleasant odor of butyric acid makes it socially unacceptable, and makes isolation of the patients desirable. Thus, although the antineoplastic activity of butyric acid/salts has been known for many years, the foregoing disadvantages have delayed or prevented its clinical application.

In order to overcome such disadvantages, the present invention provides derivatives of butyric acid which will be defined hereinbelow, and which have been found to inhibit proliferation, and to stimulate differentiation of malignant cells. These effects are unpredictably greater than those observed for butyric acid/salts. The derivatives provided by the invention can be utilized in greatly reduced amounts, compared with the parent acid or salts thereof. Thus, in the method of treatment, intermittent injection, or oral administration of the encapsulated drug (for example) can replace administration by continuous infusion. It should therefore be possible to reduce or prevent the need for hospitalization during the term of the patient's treatment. Because of the drug potency, fluid overload and alkalosis will be reduced or eliminated and the extent of odor unpleasantness will also be considerably reduced.

While the present invention is not to be regarded as restricted by any theory of action, nevertheless it is presently believed that the esters of the invention, because of their lipophilic character, are able to penetrate the lipoproteinic membranes of cells more efficiently than the relatively polar butyric acid or its salts, and that their lessened polar character causes a delay in their rate of metabolization, which results in further amplification of the physiological effects. It is moreover believed that under the influence of hydrolytic enzymes, the present derivatives undergo hydrolytic cleavage in vivo, releasing butyric acid and other non-toxic residues.

To the best of the inventors' belief, the compounds provided by the present invention are novel, with the exception of compounds having the formula Pr—C(=O)—O—CHR"—O—(O=)C—Pr, in which R" is hydrogen or methyl (see U.S. Pat. No. 4012526). These compounds are reported to promote animal growth when used as components of animal feeds, and to prevent fungal attack on such feeds, but do not appear to have been suggested for use as components of pharmaceutical compositions. The use of such compounds as antitumor agents is therefore also unknown.

SUMMARY OF THE INVENTION

The present invention accordingly provides compounds of formulae

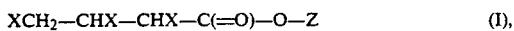

$$XCH_2-CHX-CHX-C(=O)-O-Z \qquad (I),$$

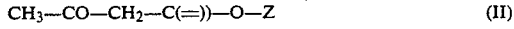

$$CH_3-CO-CH_2-C(=O)-O-Z \qquad (II)$$

and

CH$_3$—CH$_2$—CO—C(=O)—O—Z   (III), wherein X is H, or one X only may be OH; Z is —CHR—O—(O=)C—R' or

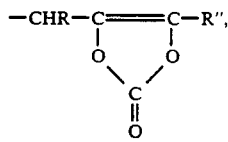

and either R represents hydrogen, alkyl, aralkyl or aryl, and R' represents alkyl, aminoalkyl, amino(substituted alkyl). aralkyl, aryl. alkoxy, aralkoxy or aryloxy, provided that in (I) when X is H and R' is propyl, then R is alkyl which contains at least two carbon atoms, aralkyl and aryl, or R and R' together constitute a single bivalent radical whereby the compounds of formula (I) include an oxygen-containing heterocyclic ring; and R" represents hydrogen, alkyl, aralkyl or aryl.

In another aspect, the invention provides pharmaceutical compositions for producing an antitumor or immune response modulating effect and which contain at least one compound of formulae XCH$_2$—CHX—CHX—C(=O)—O—Z (I'), (II) and (III); (II) and (III) being as defined above, and wherein in formula (I'), X is H or one X only may be OH, Z is —CHR—O—(O=)C—R' or

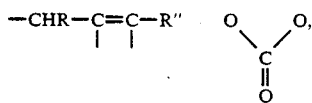

and either R represents hydrogen, alkyl, aralkyl or aryl, and R' represents alkyl, aminoalkyl, amino(substituted alkyl), aralkyl, aryl, alkoxy, aralkoxy and aryloxy, or R and R' together constitute a single bivalent radical whereby the compounds of formula (I') include an oxygen-containing heterocyclic ring, and R" represents hydrogen, alkyl, aralkyl or aryl, together with at least one pharmaceutically acceptable adjuvant, diluent or carrier. The invention further relates to a method of treating tumors or producing an immune response modulating effect in animals, which comprises administering to an animal an effective antitumorogenic or immune response modulating dose of at least one compound of formulae (I'), (II) and (III) as just defined, and to the use of a compound of formulae (I'), (II) and (III) as defined in the foregoing paragraph for the manufacture of a medicament for treating tumors in animals.

DETAILED DESCRIPTION OF THE INVENTION

In the compounds of formulae (I), (I'), (II) and (III). and in the pharmaceutical compositions which contain compounds defined with respect to formula (I'), (II) and (III), it is preferred that alkyl radicals, including those which form part of alkoxy, aralkyl and aralkoxy radicals contain no more than about 20 carbon atoms. Such alkyl radicals may be straight chain, branched chain or cyclic, as e.g. methyl, ethyl, propyl, isopropyl, butyl, isobutyl, secondary butyl, tertiary butyl, hexyl, cyclohexyl, heptyl, octyl, decyl, dodecyl or octadecyl. Aryl radicals, including those which form part of aralkyl, aryloxy and aralkoxy radicals, may be substituted or not, and may be carbocyclic or heterocyclic, such as e.g. phenyl, naphthyl, furyl or thienyl; substituents when present may be selected from, e.g., alkyl, alkoxy and halogen.

Moreover, in the compounds of formulae (I), (I'), (II) and (III), and in the pharmaceutical compositions which contain compounds defined with respect to formulae (I), (I'), (II) and (III), it is intended that when R represents hydrogen, alkyl, aralkyl or aryl, and R' represents aminoalkyl, amino(substituted alkyl), then this definition of R' includes the case when the entity —(O=)C—R' is the acyl radical of a naturally occurring amino acid, such as (by way of example only), glycine, alanine, phenylalanine or valine.

In the compounds of formulae (I), (II) and (III), which per se constitute part of the present invention, it is preferred according to one embodiment, that R is hydrogen, methyl, ethyl, propyl, isopropyl, butyl, isobutyl, secondary butyl or tertiary butyl, and that R' is methyl, ethyl, propyl, isopropyl, butyl, isobutyl, secondary butyl, tertiary butyl, methoxy, ethoxy, propoxy, isopropoxy, butoxy, isobutoxy, secondary butoxy or tertiary butoxy, provided that when R' is propyl, then R is ethyl, propyl, isopropyl, butyl, isobutyl, secondary butyl or tertiary butyl.

In accordance with one embodiment of the invention, in the compounds of formulae (I) [or (I')], (II) and (III), R and R' together constitute a single bivalent radical selected from —CH$_2$CH$_2$O—, —CH$_2$CH$_2$CH$_2$O—and o-phenylene.

In the pharmaceutical compositions of the invention, wherein the active ingredient has the formula (I') as defined herein, the preferences for R and R' set forth above also apply, and are of course not subject to the proviso. Otherwise, the pharmaceutical compositions of the invention may be adapted for oral, parenteral or rectal administration, and may be in unit dosage form, as is well known to those skilled in the pharmaceutical art.

As previously stated, the invention further relates to a method of treating tumors or producing an immune response modulating effect in animals, which comprises administering to an animal an effective antitumorogenic or immune response modulating dose of at least one compound of formula (I') as defined herein (e.g. in the form of a pharmaceutical composition of the invention), and to the use of a compound of formula (I') for the manufacture of a medicament for treating tumors or for producing an immune modulating response in animals. It is presently contemplated that the compounds described herein will be effective in both human and non-human animals.

The esters provided by the present invention may be prepared generally by any method known in the art for formation of an ester group or (when R' represents alkoxy, aralkoxy or aryloxy) of a carbonate group. For example, butyric acid may be reacted with a reagent of formula Y—CHR—O—(O=)C—R' in presence of a base, where Y is a leaving group such as halogen. methanesulfonate or p-toluenesulfonate, and R and R' are as previously defined. The base may be e.g. a trialkylamine. pyridine or an alkali metal carbonate. The reaction may be carried out in absence or in presence of an inert solvent. When a solvent is used, this may be, for example, acetone, ether, benzene, toluene, tetrahydrofuran, ethyl acetate, acetonitrile, dimethylformamide, dimethyl sulfoxide, chloroform, dioxan or 1,2-dichloroethane.

When in (I) and (I'), X=H and R' =Pr, the compounds may be prepared by an alternative process by reacting two moles of butyric acid with one mole of the corresponding aldehyde R—CHO, in presence of a catalyst such as boron trifluoride. aluminum trichloride, tin dichloride or zinc chloride.

Insofar as in compounds of formula (I), one X may be OH, the invention includes the compounds of formulae HOCH$_2$—CH$_2$—CH$_2$—C(=O)—O—Z, CH$_3$—CHOH—CH$_2$—C(=O)—O—Z and CH$_3$—CH$_2$—CHOH—C(=O)—O—Z, where Z has the significance described previously.

The compounds of the present invention in which —(O=)C—R' is the acyl radical of a naturally occurring amino acid, may be prepared for example by standard procedures such as those described by Wheeler, J. Med. Chem., 22:657 (1979), which is incorporated herein by reference.

Preparation of the esters of the invention will be illustrated by the following non-limitative examples.

EXAMPLE I

Pivaloyloxymethyl butyrate

To a mixture of butyric acid (5.7 ml., 40 mmol.) and chloromethyl pivalate (18 ml., 1 mmol.) in acetone (10 ml.) is added triethylamine (12.17 ml., 88 mmol.). The reaction mixture is stirred at room temperature for 24 hours, it is then evaporated and the residue is treated with a mixture of water and ethyl acetate. The organic phase is separated, dried over potassium carbonate, filtered and evaporated. The residue is fractionally distilled, to give the title compound (4.42 g., yield 57%). b.p. 88°-93° C./2 mm. $^1$H-NMR ppm (CDCl$_3$): 5.753 (s, 2H). 2.336 (t, 2H), 1.670 (sextet, 2H), 1.213 (s. 9H). 0.953 (t, 3H).

EXAMPLE II

Ethylidene dibutyrate

To ice-cooled BF$_3$-etherate (8.66 g.. 61 mmol.) is added dropwise via a syringe, over one hour, a mixture of butyric anhydride (6.58 g., 41.6 mmol.) and acetaldehyde (1.22 g., 27.7 mmol.). The reaction mixture is stirred for an additional 2 hours, 10% aq. sodium acetate solution (28 ml.) is added, and the mixture again stirred for 45 minutes. The oily layer is extracted into ether (2×25 ml.), and the combined ethereal extracts are washed with saturated aqueous sodium bicarbonate solution until no further evolution of CO$_2$ is observed. The organic phase is then washed with water, dried over magnesium sulfate, filtered, concentrated and the residue is fractionally distilled at 8-12 mm. Hg, the fraction distilling at up to 62° C. being collected. Yield 2.18 g. (39%). $^1$H H-NMR ppm (CDCl$_3$): 6.88 (q. J=5.6 Hz, 1H), 2.30 (dt, J=0.75, 7.5 Hz. 4H), 1.65 (sextet. J=7.5 Hz. 4H). 1.47 (d. J=5.5 Hz, 3H). 0.95 (t, J=7.5 Hz, 6H).

EXAMPLE III

Butylidene dibutyrate

The title compound is prepared by the same procedure as that described in Example II, but replacing the acetaldehyde by butyraldehyde. Yield 37%, b.p. 125°-135° C./12-15 mm. Hg. $^1$H-NMR ppm (CDCl$_3$): 6.82 (t, J=5.6 Hz, 1H), 2.30 (m, 4H), 1.75 (m, 2H). 1.65 (sextet, J=7.5 Hz, 4H), 1.40 (q, J=7.5 Hz, 2H). 0.953 and 0.949 (2t, J=7.5 Hz, 9H).

EXAMPLE IV (1-Butyroxy)ethyl ethyl carbonate

To a solution of butyric acid (0.58 g., 6.55 mmol.) and 1-chloroethyl ethyl carbonate (1 g., 6.55 mmol.) in acetonitrile (15 ml.) is added water (2 drops), benzyltrimethylammonium hydroxide (2 drops of 40% aqueous solution) and potassium hydroxide (0.44 g., 7.86 mmol.). The reaction mixture is stirred under reflux for 4 hours, it is filtered, and ether is added to the filtrate. The combined organic phase is thrice washed with water, dried over magnesium sulfate and filtered. The filtrate is concentrated in vacuo and the residue is distilled at 75° C. in a Kugelrohr apparatus at 0.1 mm. Hg. Yield 0.57 g. (42.7%). VPC chromatography on a 4 m, 20% Carbowax 20M on Chromosorb WAW, temperature 110° C., flow rate 65 ml./min., gave a retention time of 66.6 minutes. $^1$H-NMR ppm (CDCl$_3$): 6.77 (q. J=5 Hz, 1H), 4.22 (q. J=7 Hz, 2H), 2.32 (t, J=7.5 Hz, 2H), 1.66 (sextet, J=7.5 Hz, 2H), 1.52 (d, J=5.5 Hz. 3H), 1.318 (t, J=7.5 Hz, 3H). 0.95 (t. J=7.5 Hz, 3H).

EXAMPLE V (3-Butyroxy)phthalide

To a solution of butyric acid (1.10 g., 12.5 mmol.) in dimethylformamide (13 ml.) is added triethylamine (1.78 g., 17.6 mmol.) and 3-chlorophthalide (2.10 g., 12.5 mmol.). The reaction mixture is stirred for 8 days, ethyl acetate (40 ml.) is added and the mixture is filtered. The filtrate is washed with 4×15 ml. water, dried over magnesium sulfate, filtered and concentrated in vacuo. Yield 2.28 g. (82.8%). $^1$H-NMR ppm (CDCl$_3$): 7.93 (dd, J=0.7. 7.5 Hz, 1H), 7.76 (dt, J=1.1, 7.5 Hz, 1H), 7.65 (dt, J=1.0, 8.2 Hz, 1H), 7.58 (dd, J=0.7, 8.2 Hz, 1H), 7.46 (s, 1H), 2.42 (t, J=7.4 Hz, 2H), 1.72 (sextet, J=7.4 Hz, 2H), 0.99 (t, J=7.4 Hz, 3H).

BIOLOGICAL RESULTS

The compound of the invention prepared in Example I gave the results indicated in paragraphs (a), (b) and (c), below, when tested on: (i) leukemic cells from six myeloid leukemic patients, and (ii) promyelocytic cell line HL-60.

(a) Cytotoxicity. The viability of the cells 60 hours after exposure was determined by Trypan Blue exclusion. The concentrations which resulted in 50% inhibition (LD$_{50}$) were as follows:

|  | Cells | |
| --- | --- | --- |
|  | (i) | (ii) |
| Compound of Example I | 0.15 mM | 0.1 mM |
| Butyric acid/salts | 1.00 mM | 0.4 mM |

(b) Inhibition of cell proliferation. This was evaluated by inhibition of tritiated thymidine incorporation. The results in the following table are self-explanatory:

|  | % inhibition of tritiated thymidine incorporation by compound of Example I | | |
| --- | --- | --- | --- |
|  | cells (i)* | | cells (ii)** |
| Time of exposure | 0.1 mM | 0.2 mM | 0.5 mM |
| 0.5 hr. | n.d. | n.d. | 52% |

-continued

| Time of exposure | % inhibition of tritiated thymidine incorporation by compound of Example I | | |
|---|---|---|---|
| | cells (i)* | | cells (ii)** |
| | 0.1 mM | 0.2 mM | 0.5 mM |
| 15 hrs. | 88% | 99% | 99% | n.d. = not determined
*butyric acid/salts for 24 hours caused no inhibition up to 2 mM
**butyric acid/salts for 24 hours caused no inhibition up to 1 mM In a further experiment, cells (ii) were incubated with the compound of Example I or with sodium butyrate. After a period of time as specified in the following table, the agents were removed by washing the cells, and thymidine incorporation was measured 15 hours after the end of incubation. The results were as follows:

| Time of incubation (hours) | % inhibition of tritiated thymidine incorporation by 0.5 mM compound | |
|---|---|---|
| | compound of Example I | sodium butyrate |
| 0.5 | 52 | 0 |
| 3.0 | 92 | 0 |
| 16.0 | 99 | 0 |
| 24.0 | 99 | 22 |
| 48.0 | 99 | 50 |
| 62.0 | 99 | 94 |

These results are attributed to the higher degree of permeability of the cell membrane to the compounds provided by the invention, than the permeability of the cell membrane to butyric acid/salts. This hypothesis is also supported by uptake experiments conducted with the respective radiolabelled compounds.

(c) Induction of cytodifferentiation. This was evaluated by reduction of nitro blue tetrazolium (NBT), which is indicative of functional maturity of leucocytes. Results are indicated in the following table:

| Time of incubation (hours) | NBT reduction (% of positive cells) by 0.15 mM compound | |
|---|---|---|
| | compound of Example I | sodium butyrate |
| 24 | 24 | 11 |
| 48 | 49 | 29 |
| 72 | 66 | 48 |
| 96 | 77 | 66 |

These results indicate the faster action and higher potency of the compounds provided by the present invention as compared with butyric acid/salts.

In a study of colony stimulating factors (CSF) production, human lymphocytes were incubated for 72 hours with phytohemagglutinin (PHA) or the compound of Example 1, while murine splenocytes were incubated for 24 hours with concanavalin A (con A) or the compound of Example 1. CSF activity was assayed by the ability of the supernatants from these cultures to support development on semisolid agar of CFU-GM (colony forming units—granulocytes and macrophages) from bone marrow cells of BALB/c mice. Representative and reproducible experiments which are shown in the following table demonstrate that the compound of Example I stimulates CSF production by human and murine lymphocytes. Since CSF(s) are known to stimulate the immune system, the results, shown in the following table, indicate that the present compounds possess activity as immune response modulators.

| CSF production by | stimulant | Experiment 1* # CFU-GM % | | Experiment 2* # CFU-GM % | |
|---|---|---|---|---|---|
| human lymphocytes (72 hours incubation) | PHA 125 ng./ml. | 29 | 100 | 41 | 100 |
| | **20 μM | 10 | 33 | 43 | 105 |
| | **50 μM | 3 | 10 | 16 | 39 |
| mouse spleen cells (24 hours incubation) | ConA 125 ng./ml. | 104 | 100 | | |
| | **20 μM | 11 | 10 | | |
| | **50 μM | — | 0 | | |

*Experiments 1 and 2 were conducted independently
**compound of Example 1

Moreover, the in vivo efficacy of the compound of the invention prepared in Example I was tested according to protocols adopted from the "Developmental Therapeutics Program, Division of Cancer Treatment, National Cancer Institute", NIH Publication 84–2635, using the following animal models: (1) 3B131 Intraperitoneally (i.p.) implanted B16 Melanoma; (2) 3B132 Subcutaneously (s.c.) implanted B16 Melanoma: and (3) 3LL32 Subcutaneously (s.c.) implanted Lewis Lung Carcinoma. Results according to the following table were obtained.

| animal model | compound administered (mg./kg./mouse, i.p.) | | treatment injection schedule | ILS % |
|---|---|---|---|---|
| (1) | * | 250 | 1–9 days, daily | 154 |
| | cisplatin | 1.5 | 1–9 days, daily | 164 |
| (2) | * | 125 | 1–6 days, daily | 150 |
| (3) | * | 125 | 1–6 days, daily | 152 |
| | * | 125 | 1–18 days, every odd day | 186 |
| | cytoxan | 100 | day 1 only | 152 |

*compound of Example 1
ILS = increased life span compared to untreated animals

The results in the above table demonstrate that the compound of Example 1 is an effective chemotherapeutic agent, in animal models.

Using standard procedures, the therapeutic index ($LD_{50}/ED_{50}$) of the compound of Example 1 was determined to lie within the range 15–20.

It is postulated that the butyrate esters provided by the invention undergo intracellular hydrolysis to butyric acid; the residual fragments of the hydrolysis would be non-toxic. We have found that in the particular case of the compound of Example I, where the hydrolysis product is expected to be pivalic acid, the latter per se shows no activity under conditions in which the parent compound of the invention was active. An alternative metabolic route may involve (where appropriate) the oxidation of butyrates to hydroxy-butyrates and/or oxo-butyrates.

Moreover, it may be noted that the alcohol fragments of the esters provided by the present invention are analogous to those found in clinically approved drugs such as pivampicillin [von Daehne et al. J. Med. Chem., 13:6070 (1970)]; bacampicillin [Bodin et al. Antimicrob. Ag. Chemother. 8:5180 (1975)]; talampicillin [Clayton et al. Antimicrob. Ag. Chemother. 5:6700 (1974)]; pivcephalexin [Foresta et al, Arzneimittel-Forsch. 27:8190 (1977); pivmecillinam, bacmecillinam [Roholt, Antimicrob. Chemother. 3 (suppl. B):710 (1977). No toxic effects stemming from the hydrolysis of such esters has been reported.

ADVANTAGES OF THE INVENTION

The compounds provided by the invention are preferred to butyric acid/salts as antineoplastic agents (in addition to the fact that they generally overcome the disadvantages of the latter as mentioned hereinabove). for the reasons that they are active at considerably lower concentrations; they elicit their antineoplastic activity at least 100 times faster; and that they penetrate the cell membranes at a much greater rate. The compounds are thus highly potent and moreover they display low host toxicity.

As already mentioned, the compounds of the invention also appear to have immune response modulating activity, besides the antitumorogenic activity. These properties are valuable in the treatment of immunodeficient diseases.

While specific embodiments of the invention have been particularly described, it will be appreciated by those skilled in the art that many variations and modifications may be made. The invention is accordingly not to be construed as limited to such embodiments, rather the invention is defined only by the claims which follow.

We claim:

1. Compounds selected from the group consisting of compounds having formulas (I), (II) and (III):

$$XCH_2-CHX-CHX-C(=O)-O-Z \quad (I),$$

$$CH_3-CO-CH_2-C(=O)-O-Z \quad (II) \text{ and}$$

$$CH_3-CH_2-CO-C(=O)-O-Z \quad (III)$$

wherein X is H, or one X only may be OH; Z is $-CHR-O-(O=)C-R^1$, R represents a member selected from the group consisting of hydrogen and alkyl, and R' represents a member selected from the group consisting of alkyl, aminoalkyl, aralkyl, aryl, alkoxy, aralkoxy and aryloxy, in which aryl by itself, and aryl in aralkyl, aralkoxy and aryloxy, are each selected from the group consisting of sub-groups (a) and (b), wherein (a) is unsubstituted phenyl, naphthyl, furyl or thienyl, and (b) is phenyl, naphthyl, furyl or thienyl, each of which is substituted by at least one substituent selected from the group consisting of alkyl, alkoxy or halogen, provided that in (I) when X is H and R' is propyl, then R is alkyl which contains at least three carbon atoms.

2. Compounds of any of the formulae depicted in claim 1, wherein R represents a member selected from the group consisting of hydrogen, methyl, ethyl, propyl, isopropyl, butyl, isobutyl, secondary butyl and tertiary butyl.

3. Compounds according to claim 1, wherein R' represents a member selected from the group consisting of methyl, ethyl, propyl, isopropyl, butyl, isobutyl, secondary butyl, tertiary butyl, methoxy, ethoxy, propoxy, isopropoxy, butoxy, isobutoxy, secondary butoxy and tertiary butoxy, provided that in formula (I) when X is H and R' is propyl, then R is a member selected from the group consisting of propyl, isopropyl, butyl, isobutyl, secondary butyl and tertiary butyl.

4. Pharmaceutical compositions for producing at least one effect selected from an antitumor effect and an immune response modulating effect, and which contain at least one compound selected from the group consisting of compounds having formulae (I), (II), and (III) as defined in claim 1, together with at least one pharmaceutically acceptable adjuvant, diluent or carrier.

5. Pharmaceutical compositions according to claim 4, wherein R represents a member selected from the group consisting of hydrogen, methyl, ethyl, propyl, isopropyl, butyl, isobutyl, secondary butyl and tertiary butyl.

6. Pharmaceutical compositions according to claim 4, wherein R' represents a member selected from the group consisting of methyl, ethyl, propyl, isopropyl, butyl, isobutyl, secondary butyl, tertiary butyl, methoxy, ethoxy, propoxy, isopropoxy, butoxy, isobutoxy, secondary butoxy and tertiary butoxy.

7. Pharmaceutical compositions according to claim 4, and which are adapted for oral, parenteral or rectal administration.

8. Pharmaceutical compositions according to claim 4, and which are in unit dosage form.

9. A method of treating tumors in animals, which comprises administering to an animal an antitumorogenic effective dose of at least one compound selected from the group consisting of compounds having any of the formulae (I), (II) and (III), as defined in claim 1.

10. A method according to claim 9, wherein at least one compound is administered in the form of a pharmaceutical composition which comprises at least one pharmaceutically acceptable adjuvant, diluent or carrier.

11. A method to claim 9, wherein the manner of administration is intermittent injection.

12. Pivaloyloxymethyl butyrate.

* * * * *

UNITED STATES PATENT AND TRADEMARK OFFICE
CERTIFICATE OF CORRECTION

PATENT NO. : 5,200,553

DATED : April 6, 1993

INVENTOR(S) : Abraham NUDELMAN, Matitiahu SHAKLAI, Ada REPHAELI

It is certified that error appears in the above-identified patent and that said Letters Patent is hereby corrected as shown below:

On the Title page, add the following co-Assignee:

[73] Assignee: Bar Ilan University,
    52 100 Ramat Gan, Israel

Signed and Sealed this

Twelfth Day of April, 1994

*Attest:*

BRUCE LEHMAN

*Commissioner of Patents and Trademarks*

*Attesting Officer*

UNITED STATES PATENT AND TRADEMARK OFFICE
CERTIFICATE OF CORRECTION

PATENT NO. : 5,200,553
DATED : April 6, 1993
INVENTOR(S) : Abraham Nudelman, Matitiahu Shaklai, Ada Rephaeli It is certified that error appears in the above-indentified patent and that said Letters Patent is hereby corrected as shown below:

On the Title page, add the following Item

[73] Assignee: Bar Ilan University,
52 100 Ramat Gan, Israel

Signed and Sealed this

Twelfth Day of November, 1996

*Attest:*

BRUCE LEHMAN

*Attesting Officer*     *Commissioner of Patents and Trademarks*